United States Patent [19]
Lattin et al.

[11] Patent Number: 5,551,953
[45] Date of Patent: Sep. 3, 1996

[54] ELECTROTRANSPORT SYSTEM WITH REMOTE TELEMETRY LINK

[75] Inventors: Gary A. Lattin, Forest Lake, Minn.; Thomas A. Riddle, Sunnyvale, Calif.

[73] Assignee: Alza Corporation, Palo Alto, Calif.

[21] Appl. No.: 332,322

[22] Filed: Oct. 31, 1994

[51] Int. Cl.$^6$ .................... A61N 1/30; A61M 11/00
[52] U.S. Cl. ................ 604/20; 604/19; 604/50; 128/769
[58] Field of Search ................ 604/19, 20, 30, 604/50, 4, 890.1, 891.1; 128/736, 782, 769, 903

[56] References Cited

U.S. PATENT DOCUMENTS

| | | | |
|---|---|---|---|
| 3,991,755 | 11/1976 | Vernon et al. | 128/172.1 |
| 4,141,359 | 2/1979 | Jacobsen et al. | 128/172.1 |
| 4,317,457 | 3/1982 | Guillot | 128/783 |
| 4,474,570 | 10/1984 | Ariura et al. | 604/20 |
| 4,494,950 | 1/1985 | Fischell | 128/903 |
| 4,541,431 | 9/1985 | Ibrahim et al. | 607/30 |
| 4,559,037 | 12/1985 | Franetzki et al. | 604/151 |
| 4,585,652 | 4/1986 | Miller et al. | 424/83 |
| 4,619,653 | 10/1986 | Fischell | 604/891 |
| 4,639,244 | 1/1987 | Rizk et al. | 604/19 |
| 4,819,657 | 4/1989 | Kraft et al. | 128/736 |
| 4,981,141 | 1/1991 | Segalowitz | 128/903 |
| 5,006,108 | 4/1991 | La Prade | 604/20 |
| 5,011,472 | 4/1991 | Aebischer et al. | 604/50 |
| 5,036,861 | 8/1991 | Sembrowich et al. | 604/20 |
| 5,047,007 | 9/1991 | McNichols et al. | 604/20 |
| 5,059,175 | 10/1991 | Hanover et al. | 604/891.1 |
| 5,108,363 | 4/1992 | Tuttle et al. | 604/20 |
| 5,160,316 | 11/1992 | Henley | 604/20 |
| 5,167,625 | 12/1992 | Jacobsen et al. | 604/891.1 |
| 5,167,626 | 12/1992 | Casper et al. | 604/93 |
| 5,169,384 | 12/1992 | Bosniak et al. | 604/20 |
| 5,170,801 | 12/1992 | Casper et al. | 128/769 |
| 5,224,927 | 7/1993 | Tapper | 604/20 |
| 5,224,928 | 7/1993 | Sibalis et al. | 604/20 |
| 5,246,418 | 9/1993 | Haynes et al. | 604/20 |
| 5,254,081 | 10/1993 | Maurer et al. | 604/20 |
| 5,309,919 | 5/1994 | Snell et al. | 128/697 |
| 5,380,271 | 1/1995 | Gyory | 604/20 |

FOREIGN PATENT DOCUMENTS

| | | | |
|---|---|---|---|
| 0526166A2 | 2/1993 | European Pat. Off. | G06F 15/42 |
| 4028125A1 | 7/1991 | Germany | A61N 1/30 |
| WO9221307 | 12/1992 | WIPO | A61F 7/12 |
| WO9314812 | 8/1993 | WIPO | A61N 1/30 |

*Primary Examiner*—Angela D. Sykes
*Assistant Examiner*—Stephen Huang
*Attorney, Agent, or Firm*—D. Byron Miller; Felissa H. Cagan; Steve F. Stone

[57] ABSTRACT

An electrotransport system (20) for delivering a therapeutic agent (36) through a body surface (40) (eg, skin) of a patient includes a pair of electrodes (34, 38) for contacting the body surface, at least one of which contains the therapeutic agent (36). The system (20) is physically separated into a control unit (22) and a delivery unit (24) connected by a radiated energy signal-based telemetry link. The telemetry link may be radio frequency, ultrasonic, optical, infrared or inductively coupled. Signals from the control unit may be transmitted to the delivery unit by the telemetry link, or vice versa. The delivery unit may control electrotransport current on the signal transmitted. The radiated energy signal may be encoded to improve immunity to extrinsic interference. The delivery unit (24) may be configured with sensor means for detecting a condition such as a body or system parameter reaching some predetermined limit. The delivery unit (24) may also have an additional telemetry link connecting to the control unit (22) for transmitting the system or body status condition to the control unit. Visual or audio indicators may be provided on the control unit (22) for indication of system or body status conditions detected and transmitted by the delivery unit (24).

21 Claims, 2 Drawing Sheets

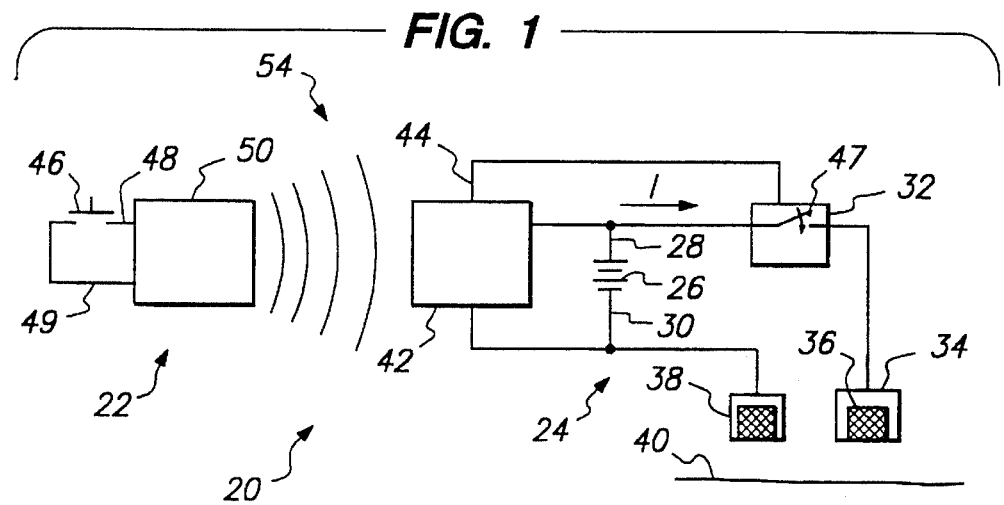
FIG. 1
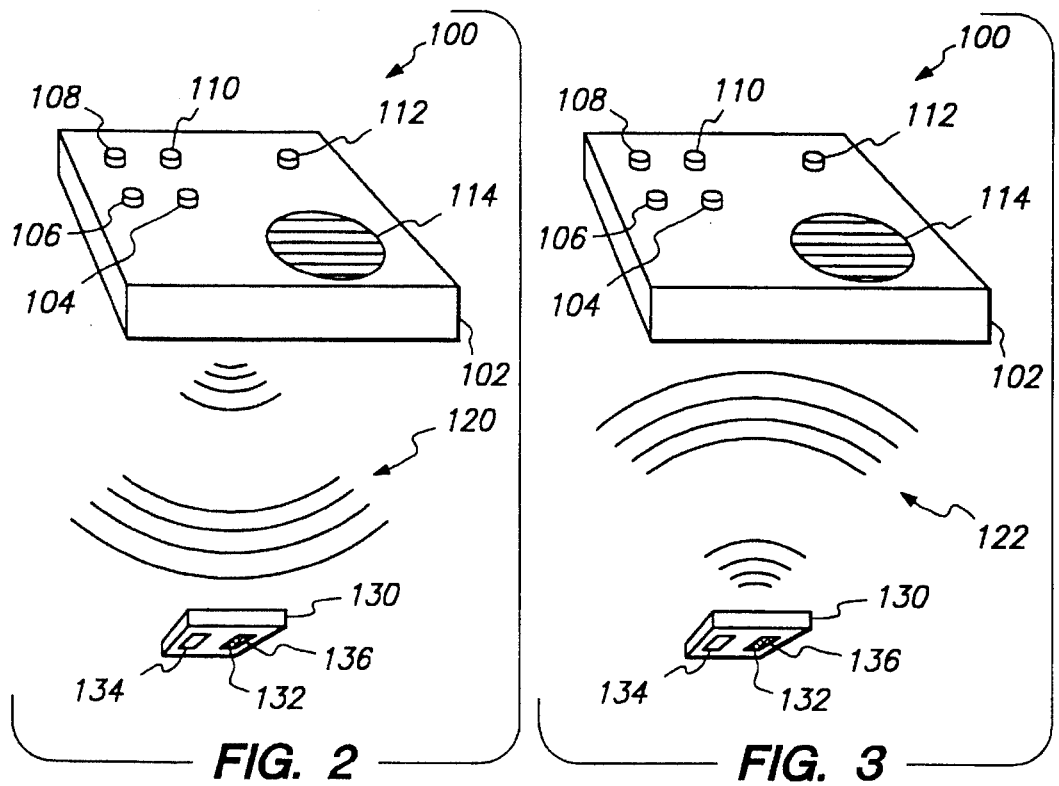
FIG. 2
FIG. 3

ELECTROTRANSPORT SYSTEM WITH REMOTE TELEMETRY LINK

TECHNICAL FIELD

This invention relates to electrotransport devices for delivering a therapeutic agent (eg, a drug), which devices have telemetry means for communicating between agent delivery means and remote controlling means for controlling and receiving parameters of therapeutic agent electrotransport delivery.

BACKGROUND ART

The term "electrotransport" as used herein refers generally to the delivery of an agent (eg, a drug) through a membrane, such as skin, mucous membrane, or nails. The delivery is induced or aided by application of an electrical potential. For example, a beneficial therapeutic agent may be introduced into the systemic circulation of a human body by electrotransport delivery through the skin. A widely used electrotransport process, electromigration (also called iontophoresis), involves the electrically induced transport of charged ions. Another type of electrotransport, electroosmosis, involves the flow of a liquid, which liquid contains the agent to be delivered, under the influence of an electric field. Still another type of electrotransport process, electroporation, involves the formation of transiently-existing pores in a biological membrane by the application of an electric field. An agent can be delivered through the pores either passively (ie, without electrical assistance) or actively (ie, under the influence of an electric potential). However, in any given electrotransport process, more than one of these processes may be occurring simultaneously to a certain extent. Accordingly, the term "electrotransport", as used herein, should be given its broadest possible interpretation so that it includes the electrically induced or enhanced transport of at least one agent, which may be charged, uncharged, or a mixture thereof, whatever the specific mechanism or mechanisms by which the agent actually is transported.

Electrotransport devices use at least two electrodes that are in electrical contact with some portion of the skin, nails, mucous membrane, or other surface of the body. One electrode, commonly called the "donor" or "active" electrode, is the electrode from which the agent is delivered into the body. The other electrode, typically termed the "counter" or "return" electrode, serves to close the electrical circuit through the body. For example, if the agent to be delivered is positively charged, ie, a cation, then the anode is the active or donor electrode, while the cathode serves to complete the circuit. Alternatively, if an agent is negatively charged, ie, an anion, the cathode is the donor electrode. Additionally, both the anode and cathode may be considered donor electrodes if both anionic and cationic agent ions, or if uncharged or neutrally charged agents, are to be delivered.

Furthermore, electrotransport delivery systems generally require at least one reservoir or source of the agent to be delivered, which is typically in the form of a liquid solution or suspension. Examples of such donor reservoirs include a pouch or cavity, a porous sponge or pad, and a hydrophilic polymer or a gel matrix. Such donor reservoirs are electrically connected to, and positioned between, the anode or cathode and the body surface, to provide a fixed or renewable source of one or more agents or drugs. Electrotransport devices also have an electrical power source such as one or more batteries. Typically, one pole of the power source is electrically connected to the donor electrode, while the opposite pole is electrically connected to the counter electrode. In addition, some electrotransport devices have an electrical controller that controls the current applied through the electrodes, thereby regulating the rate of agent delivery. Furthermore, passive flux control membranes, adhesives for maintaining device contact with a body surface, insulating members, and impermeable backing members are other optional components of an electrotransport device.

All electrotransport agent delivery devices utilize an electrical circuit to electrically connect the power source (eg, a battery) and the electrodes. In very simple devices, such as those disclosed in Ariura et al U.S. Pat. No. 4,474,570, the "circuit" is merely an electrically conductive wire used to connect the battery to an electrode. Other devices use a variety of electrical components to control the amplitude, polarity, timing, waveform shape, etc. of the electric current supplied by the power source. See, for example, McNichols et al U.S. Pat. No. 5,047,007.

To date, commercial transdermal electrotransport drug delivery devices (eg, the Phoresor, sold by Iomed, Inc. of Salt Lake City, Utah; the Dupel Iontophoresis System sold by Empi, Inc. of St. Paul, Minn.; the Webster Sweat Inducer, model 3600, sold by Wescor, Inc. of Logan, Utah) have generally utilized a desk-top electrical power supply unit and a pair of skin contacting electrodes. The donor electrode contains a drug solution while the counter electrode contains a solution of a bio-compatible electrolyte salt. The "satellite" electrodes are connected to the electrical power supply unit by long (eg, 1–2 meters) electrically conductive wires or cables. Examples of desk-top electrical power supply units which use "satellite" electrode assemblies are disclosed in Jacobsen et al U.S. Pat. No. 4,141,359 (see FIGS. 3 and 4); LaPrade U.S. Pat. No. 5,006,108 (see FIG. 9); and Maurer et al U.S. Pat. No. 5,254,081 (see FIGS. 1 and 2). The power supply units in such devices have electrical controls for adjusting the amount of electrical current applied through the electrodes. The "satellite" electrodes are connected to the electrical power supply unit by long (eg, 1–2 meters) electrically conductive wires or cables. Wire connections are subject to disconnection, limit patient movement and mobility and can also be uncomfortable. The wires connecting the power supply unit to the electrodes limits their separation to the length of the wires provided. It would be an advantage to retain the benefits of a remote means for controlling the operation of an electrotransport delivery device worn by a patient (eg, in a hospital ward) without the disadvantages of intervening wires.

More recently, small self-contained electrotransport delivery devices adapted to be worn on the skin, sometimes unobtrusively under clothing, for extended periods of time have been proposed. The electrical components in such miniaturized electrotransport drug delivery devices are also preferably miniaturized, and may be either integrated circuits (ie, microchips) or small printed circuits. Electronic components, such as batteries, resistors, pulse generators, capacitors, etc., are electrically connected to form an electronic circuit that controls the amplitude, polarity, timing, waveform shape, etc. of the electric current supplied by the power source. Such small self-contained electrotransport delivery devices are disclosed for example in Tapper U.S. Pat. No. 5,224,927; Sibalis et al U.S. Pat. No. 5,224,928 and Haynes et al U.S. Pat. No. 5,246,418.

With regard to providing electrical current to electrotransport electrodes, Henley U.S. Pat. No. 5,160,316 discloses a generator driving a primary isolated current loop. The current loop feeds current to individual channels in a wide area, multi-channel electrode via a plurality of individual secondary current loops. The isolated primary current loop is disposed in adjacent, but insulated alignment with the individual secondary current loops for close inductive coupling. There is no power source for the electrotransport currents except the coupled current from the isolated primary current loop. The controls and switches for the isolated primary current loop are contained in a control box connected to the primary current loop. The current loops in Henley must be very closely coupled to have efficient transfer of current. If the current loop were physically separated by a significant distance, say several feet, from the individual current loops, the control of the electrotransport current, and hence the rate of electrotransport drug delivery, would vary considerably.

One concern, particularly with small self-contained electrotransport delivery devices that are adapted to be worn on the body and/or under clothing, is the difficulty and inconvenience of using controls or reading indicators on the device. This is also a concern (ie, from the standpoint of viewing the electrotransport delivery device or to manipulate controls thereon) when the electrotransport device is worn on an inconvenient area of the body, such as the back, the upper outer arm, and the like. Also, whereas it is convenient to have very small delivery units that are unobtrusive, it is a disadvantage if the delivery unit has controls that are too small to be effectively manipulated, or indicators (eg, LED's) that are too small to be clearly seen, by a substantial portion of the population (eg, the elderly).

It may be desired, for example, to have a start button on the electrotransport device that initiates drug delivery on demand of the patient. With a small, self-contained unit, the placement of the unit on the patient's body is usually limited to a body location that the patient can both see and reach. The limited location option may interfere with the efficacy of the therapy. Thus, in certain situations it would be an advantage to separate the controls for controlling the operation of the electrotransport delivery device from the device itself.

It may also be desired to obtain some delivery system information for the benefit of the user or a medical attendant. Examples of such delivery system information include the dosing history, amount of drug remaining in the system to be delivered, battery life, whether the system is presently in a "delivery" mode or an "off" mode, etc. There have been proposals to incorporate patient monitoring features into electrotransport drug delivery devices. One example is blood glucose monitoring for an electrotransport insulin delivery device. Thus, if the sensed glucose levels become too high, the glucose level indicator would instruct the patient to activate the device to deliver insulin. Other types of patient information besides blood glucose levels could also be sensed and displayed on an electrotransport device indicator for the benefit of the patient or a medical technician. For example, application of therapeutic drugs, whether by electrotransport or more traditional (eg, oral) dosing, can sometimes cause unwanted reactions in certain patients. These reactions can take many forms, including respiratory depression, change in head rate, change in body temperature, sweating, shaking and the like. It would be advantageous to provide this system and/or patient information to a remote indicator so that the information may be read at a remote location (eg, at a central nurse's station in a hospital ward). This would enable a nurse or attendant to take action without having to check the delivery device worn by the patient, remove the patient's clothing or otherwise disturb the patient.

It would clearly be desirable to have electrotransport delivery systems available in a configuration with the controls and indicators mounted on a control unit that is remote from the delivery unit. The present invention provides the needed improvement without diminishing the intended therapeutic efficacy of the device or the therapeutic substance to be administered.

DISCLOSURE OF THE INVENTION

There is a need for an electrotransport device for administering a drug through a body surface (eg, skin), having complete freedom of placement of delivery electrodes, without compromising the ability of the patient or a medical technician to control the operation of the device.

There is also a need for an electrotransport device having improved access to controls and status indicators independent of the location of the delivery device on a patient's body.

There is a further need for a small electrotransport delivery device adapted to be worn by the patient unobtrusively (eg, under clothing) for which the control and display features are not limited by the size of the device.

The present invention is directed to an electrotransport system for delivering a therapeutic agent through the skin of a patient, that satisfies the needs described above. The electrotransport system is comprised of a control unit and a delivery unit, which two units are remote from one another and communicate with one another using telemetry. The delivery unit is adapted for mounting on the body surface (eg, skin) of a patient. The delivery unit includes a pair of electrodes, at least one of which is a "donor" electrode containing the therapeutic agent (eg, a drug) to be delivered through the body surface (eg, skin). The delivery unit also includes a source of electrical power (eg, one or more batteries) which is electrically connectable to the electrodes in order to apply an electrotransport current through the electrodes and the patient. The system is characterized by a telemetry communication link between the delivery and control units whereby the units communicate by means of a radiated energy signal transmitter means and a radiated energy signal receiver means.

In a preferred embodiment, the control unit communicates with the delivery unit in order to control the electrotransport current applied to the patient, and thereby control the delivery of the therapeutic agent to the patient. In a more preferred embodiment, the delivery unit includes a receiver means adapted for receiving a radiated energy signal which is transmitted by the control unit and providing a control signal responsive thereto. The delivery unit also includes a current control means adapted to control (eg, control the initiation, interruption, magnitude, polarity, waveform shape, pulsing frequency, and/or duty cycle) the electrotransport current applied. The current control means is responsive to the control signal from the receiver means. The control unit, which is remote from the delivery unit worn by the patient, preferably includes a transmitter means. The transmitter means is responsive to an input signal, for example, a preprogrammed and/or a manually selected input signal chosen by the operator (eg, the patient or a medical technician). Upon receiving the input signal, the transmitter means transmits a radiated energy signal (eg, an infrared signal, a radio frequency signal, or an ultrasonic signal) to the receiver means in the delivery unit, whereby the electrotransport current applied by the delivery unit is controlled by the input signal to the remote control unit.

The distance separating the control unit from the delivery unit is limited only by the strength of the transmitted radiated energy signal from the transmitter means, the signal-to-noise ratio of the receiver means and the radiated energy modulation scheme selected for the particular implementation. The distance can range from quite small (eg, several centimeters) to very large (eg, hundreds of kilometers).

The control unit may be a small, lightweight unit (eg, a wand or hand held unit) and optionally may be mounted on an easily accessible part (eg, the wrist or lower arm) of the patient's body. Alternatively, the control unit may be a larger unit (eg, desk size) with a more powerful transmitter adapted to operate within, eg, several hundred meters of the delivery unit. In such cases, the control unit may be operated from the patient's bedside or from a centralized nursing station in a hospital ward.

The control unit may optionally include a plurality of manually operated switches adapted to provide a plurality of signal inputs to the control unit for transmitting a plurality of signals to the delivery unit.

The electrotransport control unit may also optionally include a microprocessor having a plurality of inputs connected suitably to the plurality of switches. The microprocessor has an output connected to the transmitter for controlling the radiated energy signal to be transmitted. The microprocessor may have a plurality of stored programs for providing a corresponding plurality of control signals. The operator selects one of the stored programs, eg, by selecting one of a plurality of manually operated switches in order to cause the delivery unit to deliver an electrotransport current of predetermined amplitude, timing, etc, which corresponds to the operator's selection.

The telemetry link may be provided by one of a number of radiated energy transmitting and receiving means. In a preferred embodiment, the radiated energy is radio frequency (RF) radiated energy over a range of frequencies of between about 1 MHz to about 1000 MHz. The radio frequency energy may be modulated by amplitude modulation, frequency modulation, frequency shift keying, or phase shift keying. Alternatively, the radiated energy may be in the form of ultrasonic radiant energy, optical radiant energy or by the radiant energy of electromagnetic induction.

The electrotransport telemetry may include a coding and decoding means for coding the transmitted signals in a predetermined security code. Coding the transmitted signal provides additional security against falsely initiating agent delivery due to unwanted signals such as extrinsic radiant energy interference.

The electrotransport telemetry system of this invention may include a sensor means mounted in the delivery unit for sensing a predetermined patient body parameter condition, such as breathing rate, blood glucose concentration, skin resistance, body motion, muscle movement (eg, contraction), tissue oxygen content, tissue carbon dioxide content, body temperature, heart rate, sweat response or the like. The sensor means may provide a sense signal to a return radiated energy transmitter means for transmitting a return radiated energy signal to the control unit. The control unit may have a corresponding receiver for receiving the return radiated energy signal from the delivery unit. The control unit may include an indicator for displaying the sensed parameter condition by any type of conventional display means including LED, LCD display, audio annunciator or the like and in the case of a larger size control unit the indicator for displaying the sensed parameter may be a cathode ray tube, or other type of video screen, a printer or the like. Alternatively, the delivery unit may have a sensor for sensing an operating parameter of the delivery unit (eg, battery strength, whether the delivery unit is presently in a "delivery" mode or in an "off" mode, therapeutic agent dosing history, amount of therapeutic agent remaining in the delivery unit, device malfunction, etc) and transmitting the system parameter condition back to the control unit, through the return telemetry link, where it is appropriately received and displayed for the benefit of the operator. Alternatively, the delivery unit may have a patient activated switch for indicating an emergency condition which is transmitted to the control unit to set off an alarm. In addition to the patient activated alarm, the delivery unit may contain means for sensing geographical location (eg, through antenna or satellite based global positioning systems) and transmitting said location to the control unit.

One advantage of separating the control unit and the delivery unit by the telemetry link lies in the opportunity to add features to the delivery unit in the space that is otherwise unavailable if the control and delivery unit are physically combined.

BRIEF DESCRIPTION OF THE DRAWINGS

Reference is made, in the following detailed description, to FIGS. 1 to 4 in which like parts are designated by like reference numerals, and in which;

FIG. 1 is a schematic of an electrotransport delivery system having a radiated energy telemetry link between a control unit and a delivery unit.

FIG. 2 is a diagram of an electrotransport delivery system having a radiated energy telemetry link illustrating the remotely located control unit transmitting a control signal to the electrotransport delivery unit.

FIG. 3 is a diagram of an electrotransport delivery system illustrating a remotely located control unit receiving a response signal from an electrotransport delivery unit.

MODES FOR CARRYING OUT THE INVENTION

Figure 4:
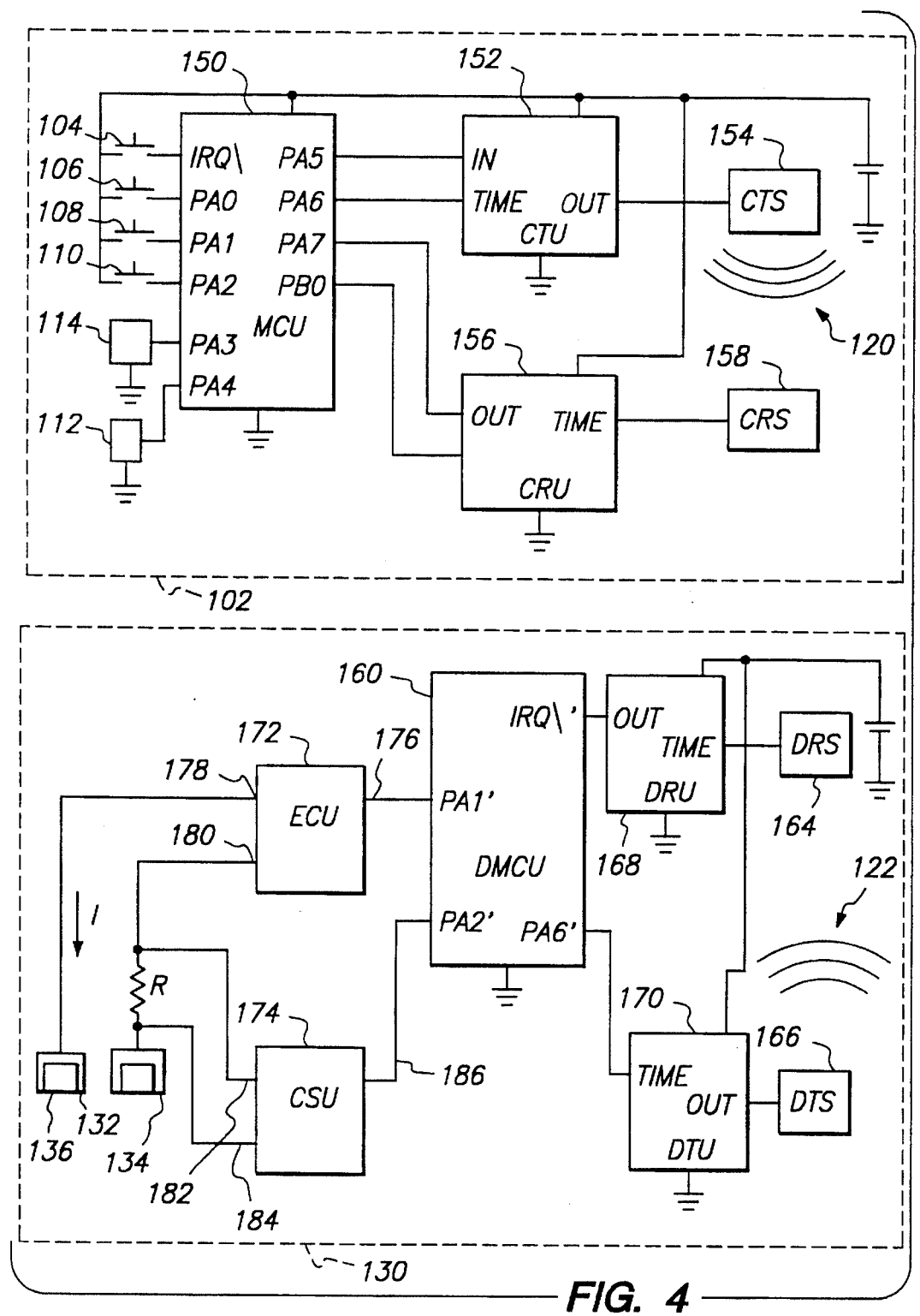
FIG. 4 is a detailed block diagram of one embodiment of a electrotransport delivery system having a telemetry link between a control unit and a delivery unit.

With reference to FIG. 1 there is shown a schematic diagram of an electrotransport system having a remote telemetry link for programming and receiving system information in accordance with this invention and generally indicated by the numeral 20. The system 20 includes a control unit indicated by the numeral 22 and a delivery unit indicated by the numeral 24. The control unit 22 and delivery unit 24 are spaced apart and electrically isolated from each other. The delivery unit 24 includes a power source 26. The source 26 provides a source connection 28 and a return connection 30 for supplying an electrotransport current, I. Switch means 32 connects in series with the power source 26 and a first electrotransport electrode 34. The first electrode 34 is configured to make contact with the skin 40 of a patient's body. The first electrode 34 contains a therapeutic agent 36, such as a drug, which is responsive to the electrotransport current I, for delivery through the skin 40. A return electrode 38 provides the return path for the current I from the skin 40. The return electrode 38 connects to the return connection 30 of the power source 26.

The power source 26, switch means 32, electrode 34, skin 40 and return electrode 38 thus form a complete circuit for the electrotransport current, I.

The delivery unit 24 includes a receiver 42. The receiver 42 is configured to receive and respond to a radiated energy signal 54 by outputting a control signal 44 upon receiving the signal 54. The control signal 44 connects to switch means 32. The switch means 32 is configured to respond to the control signal 44 by closing a switch 47 between the source 26 and the delivery electrode 34 thereby enabling electrotransport current I to flow.

The control unit 22 includes a transmitter 50 responsive to the input signal 48. Transmitter 50 produces a radiated signal 54 upon receiving an input signal 48. Closure of an input switch 46 connects input signal 48 with a second input 49 of control unit 22.

In one simple embodiment in accordance with this invention, the transmitter 50 of the control unit 22 produces the signal 54 as long as the switch 46 is closed and the input signal 48 is present. The receiver 42 outputs a control signal 44 as long as the signal 54 is being received, and the switch 47 remains closed, providing current I to deliver the therapeutic agent 36 through the patient's skin 40.

In the embodiment of FIG. 1, the agent 36 is contained in the electrode 34 connected as an anode. Other embodiments may be used, in which the agent to be delivered is contained in the cathodic electrode 38, or wherein agents are contained in both electrodes. The power source 26 is shown as a battery with only a single direct current (DC) voltage supply. It is contemplated that the power source 26 could be a combination of DC and/or alternating current (AC) sources providing complex DC and/or AC waveforms or a combination of DC levels and/or ramps as desired.

The control of electrotransport current I, is shown as a simple switch 47 of switch means 32 whereby the "control" of current, I, is simply one of on or off. Besides a simple on/off type of current control, it is contemplated that more complex control over the magnitude, polarity, waveform shape, pulsing frequency, duty cycle, etc. of the current I and dosing time may be obtained by using more complex electrotransport circuits as described below.

The switch means 32 can include a magnetically actuated reed switch in place of or in addition to the switch 47 for controlling the current, I. Reed switches have been used in implanted devices such as cardiac pacemakers. See, for example, Alferness et al, U.S. Pat. No. 4,066,086; Berntson U.S. Pat. No. 4,676,248; Hartlaub et al, U.S. Pat. No. 4,401,120, and Bowers U.S. Pat. No. 3,311,111, incorporated herein by reference. A magnetically activated reed switch provides an added means of redundancy for preventing unwanted radiated signals from causing inadvertent drug delivery by ensuring that the current, I, is not delivered unless the reed switch is closed. This can be accomplished by passing a sufficiently strong magnet (eg, in the form of a magnetic wand) over the delivery unit 24 during transmission of signal 54. Once the signal 54 is received by the delivery unit 24, the magnetic wand may be removed from its position over the unit 24 to open the reed switch to ensure that extraneous radiated energy signals have no effect on the subsequent operation of unit 24.

Similarly, with reference to FIG. 4, a magnetically actuated reed switch (not shown) can be connected in series with the connection between the OUT signal of DRU 168 and the IRQ\' signal of DMCU 160. In this case, programming signals transmitted by the transmitter CTS 154 have no effect on the programming of drug delivery by the delivery unit 130, unless the reed switch is closed. Closure of the reed switch is accomplished by passing a magnet (eg, a magnetic wand) of sufficient strength in close proximity with the reed switch. Again, this provides an additional margin of safety and immunity to extraneous radiated signals.

The delivery unit 24 may be mounted on the patients' body by conventional means, such as straps (not shown) attached to the delivery unit 24 and encircling the trunk or limb of the patient. Alternatively, the delivery unit 24 may be attached to the patients' skin by means of adhesive film around the periphery of the electrodes 34, 38. An "in-line" adhesive on the skin-contacting surfaces of electrodes 34, 38, which adhesive is permeable to the therapeutic agent 36 and other ions under the influence of the applied electric potential, may also be used to attach the delivery unit 24 to the patients' skin 40.

The physical separation and electric isolation between the control unit 22 and the delivery unit 24 provides much greater freedom in terms of separately mounting the control 22 and delivery unit 24. The delivery unit 24 may be mounted anywhere on the patient's back, neck, shoulders, head, buttocks, back of legs, under arm or other areas not easily observed or reached. The control 22 unit may be kept in any convenient location, such as strapped to the patient's wrist, in a pocket or pocketbook or elsewhere.

Radiated energy signals 54 of different types are contemplated for use in accordance with this invention. One preferred embodiment of this invention uses radio frequency (RF) signals 54 for the transmitter 50 and receiver 42 of the telemetry link. Radio frequency signals may be modulated by amplitude modulation (AM), frequency modulation (FM), frequency shift keying (FSK), phase shift keying (PSK) and the like. There is generally a trade off between modulation complexity and transmitter power consumption. AM is generally simpler but less efficient in terms of transmission range for a given power supply drain and signal to noise ratio (SNR). FM, FSK and PSK are progressively more efficient for power supply drain and SNR considerations but require progressively more complex modulation circuits. One useful reference regarding RF modulation methods is the Electronics Engineers Handbook, 3rd edition, Fink et al, McGraw Hill, New York, N.Y., 1989, chapter 14.

While the present invention is not limited to any particular frequency range, the frequency range of operation for the RF transmission is typically between about 1 MHz and 1000 MHz. One preferred frequency is about 310 MHz, corresponding to the industrial frequency band.

While the present invention is not limited to any particular power level for transmitter 50, a power level of up to 100 mW in accordance with FCC regulations is contemplated for patient operated control units (ie, in those cases where the person operating the control unit is also wearing the delivery unit). In one embodiment, a range of operation of up to about one meter was obtained with only 0.1 mW of transmitter power at a frequency of 310 MHz using coiled antennas (not shown) of about 2.5 cm diameter for the receiver 42 and about 5 cm diameter for the transmitter 50. A range of up to about 8 meters was obtained with a transmitter power of about 100 mW and similar antenna sizes.

In other embodiments of the present invention, it is contemplated that the range of operation between the control unit 22 and the delivery unit 24 may be extended up to hundreds or even thousands of kilometers, by selecting appropriate communication channels having relay links such as cellular phone networks, satellite communication links and the like.

Limiting transmitter power for the control unit 22 is not of as great concern, as the size of the control unit 22 is under fewer constraints than the size of the delivery unit 24 and therefore the control unit 22 can be made larger to accommodate larger sized batteries (in the case of a hand-held, patient-activated control unit 22), or be in the form of a table or desk sized control unit 22 which is plugged into a standard electrical outlet (in the case of a control unit 22 for controlling delivery units 24 worn by patients in a hospital ward), or be in the form of a control unit utilizing large tower-sized transmitting antenna (in the case of a control unit 22 for controlling the delivery units 24 of patients located in a particular geographic region, eg, a city or county).

Another radiated energy signal 54 contemplated for use in accordance with this invention is electromagnetic induction (EMI) using coupled coils (not shown). The coupling of radiated signals between coupled coils is determined by the mutual inductance of the coils. Calculations for the mutual inductance of coils are shown in the US Bureau of Standards Circular C74, US Government Printing Office, and Bulletin of the Bureau of Standards Vol. 8 printed 1912 and Vol. 18 printed 1918. Suitable coupled coils may be selected for transmission of radiated energy signals over a desired distance.

Yet another radiated energy signal contemplated for use in accordance with this invention, are ultrasonic waves transmitted and received by means of ultrasonic transducers. Infrared (IR) emitters and detectors may be used for radiated energy signal transmission in accordance with this invention.

With reference to FIGS. 2, 3 and 4, there is shown a particular embodiment of an electrotransport system having a telemetry link between control and delivery units in accordance with this invention and indicated generally by the numeral 100. In FIG. 2, a control unit 102 includes control buttons 104, 106, 108, and 110, an indicator LED 112 and an audio annunciator 114, such as a speaker or piezoelectric transducer. The control unit 102 transmits a radiated energy signal 120, by actuation of buttons 104–110 as explained below, to a delivery unit 130. Delivery unit 130 is positioned on the skin of a patient (not shown) by means well known in the art, such that electrotransport electrodes 132 and 134 are in contact with the patient's skin. The unit 130 provides electrotransport current, under control of the signal 120 as described below, to the electrodes 132 and 134 such that a therapeutic agent 136 contained in electrotransport electrode 132 is delivered as desired.

With reference to FIG. 3, there is depicted the delivery unit 130 transmitting a radiated response signal 122 to the control unit 102. The delivery unit 130 transmits the response signal 122 to the control unit 102 under predetermined conditions described below. The control unit 102 is configured to respond to the response signal 122 by displaying a predetermined sequence of lights on the LED 112. The control unit 102 may also be configured to respond to the response signal 122 by emitting a sequence of sounds or tones from the audio annunciator 114. In an alternate embodiment of the control unit 102, the audio annunciator 114 may be replaced by an LCD or LED display unit configured to display alphanumeric information resulting from the response signal 122.

With reference to FIG. 4, there is shown a schematic diagram of the electrotransport system 100 of FIG. 2 and 3, illustrating a preferred embodiment of a remote telemetry link between control unit 102 and delivery unit 130 for programming and control in accordance with this invention.

The control unit 102 includes a micro-controller unit (MCU) 150, a first remote-control transmitter/receiver unit (CTU) 152, a control transmitter stage (CTS) 154, a second remote-control receiver unit (CRU) 156, and a control receiver stage (CRS) 158. Indicator devices, such as audio annunciator 114 and LED 112, are also included for communicating system and/or patient status information to an operator. Power and ground connections to the individual components are made in a suitable conventional manner.

One implementation of the present invention uses a MC68HC705K1 ('705) 8-bit micro-controller, available from Motorola Semiconductor Products, Inc., Phoenix, Ariz. for the MCU 150. The '705 includes an on-chip memory with 504 bytes of erasable, programmable ROM (EPROM), 32 bytes of User RAM and a 64-bit EPROM. The '705 may be programmed to provide desired output signals on the bidirectional, software programmable pins, PA6, PA3, and PA4, and to respond to inputs on the bidirectional pins IRQ\, PA0, PA1, PA2, PA5, PA7, PB0. Switches 104, 106, 108, 110 provide inputs to pins IRQ\, PA0, PA1 and PA2, respectively.

The pin PA3 is configured as an output and connects to the audio annunciator 114. The pin PA4 is configured as an output and connects to the LED 112. The annunciator 114 and LED 112 are provided with suitable connections to the system ground of the control unit 102.

In one implementation, the MCU 150 is programmed to treat the IRQ\ input as an interrupt. A logic low level on the IRQ\ input puts the MCU 150 in a state waiting for succeeding switch actuation on inputs 106, 108, 110 to perform desired operations as described below.

The CTU 152 and CRU 156 are each TMS3637 ('3637) programmable remote-control transmitter/receiver units available from Texas Instruments, Dallas Tex. The '3637 is a remote-control transmitter/receiver. The '3637 contains 31 bits of EPROM. These 31 bits can be programmed into two groups: 22 bits to store a unique code, and 9 bits to configure the '3637 as either a transmitter or a receiver. The total number of combinations for the stored code is $2^{22}$ or 4,194,304 combinations. The CTU 152 and CRU 156 are programmed with different codes so that transmission of signals by CTS 154 and receipt of signals by CRS 158 may be securely differentiated as described in more detail below.

When the '3637 operates as a receiver, it can identify the 22-bit code for which it is programmed and consequently generates one pulse or toggles the state of an output pin, OUT. When the '3637 operates as a transmitter, it emits 22 bits of code when triggered by an external command or continuously, as long as power is applied. The programming method is described in the TMS3637 data sheet available from the Texas Instruments, Dallas, Tex. herein incorporated by reference.

The CTU 152 is programmed as a continuous mode transmitter, so that a low level on the TIME input of CTU 152 causes a continuous transmission of the 22-bit control code on the OUT pin of CTU 152 as long as the CTU 152 TIME input is low. Output PA6 of MCU 150 connects to the TIME input of CTU 152.

The MCU 150 is programmed to cause the output PA6 to remain low for a period dependent on which of the switches 106, 108, 110 were selected after switch 104. For example, the PA6 output may be programmed to provide a low level for 5, 10 or 15 minutes, depending on the selection of switch 106, 108 or 110 respectively. The MCU 150 may also be programmed to indicate which period was selected by flashing the LED 112 or beeping the annunciator 114 for a predetermined number of times, eg, 1, 2 or 3 for the 5, 10, or 15 minute period selected. This provides the operator with confirmation that the desired dosage time was selected.

The CTU 152 is programmed to output the transmitted code continuously on the OUT output of CTU 152. The CTU 152 is driven at a suitable clock rate, for example, 5.7 kHz by a clock source (not shown). The OUT signal drives the input of the CTS 154 transmitter. The CTS 154 is configured as a conventional low power AM transmitter consistent with FCC requirements to limit output power to 100 mW or less. The CTS 154 may be implemented with conventional printed circuit board and transistor technology as is well known in the art. A 2.5 cm microstrip antenna is a suitable transmitting antenna at a carrier frequency of 310 MHz. A conventional transistor LC tuned collector circuit coupled to the microstrip antenna (not shown) provides a suitable transmitter for amplitude modulation (AM) transmission in the CTS 154.

A base tuned transistor circuit (not shown) would also be a suitable transmitter stage for the CTS 154. For example, a Surface Acoustic Wave resonator such as CW SAW oscillator available from R.F. Monolithics, Inc, Dallas, Tex., may be used in the base circuit of a transmitter stage 154 and modulated by the OUT signal from CTU 152.

It is contemplated that frequency modulation (FM) would provide a lower power transmitting/receiving system for the electrotransport telemetry system 100 of this invention. It is further contemplated that Frequency Shift Keying (FSK), or Phase Shift Keying (PSK) would provide a still lower power transmitting/receiving system for the electrotransport telemetry system of this invention, at the expense of more complex modulating and demodulating circuitry.

The delivery unit 130 includes a delivery micro-controller (DMCU) 160, a delivery receiver stage (DRS) 164, a delivery transmitter stage (DTS) 166, a delivery remote-control receiver unit (DRU) 168, a delivery remote-control transmitter unit (DTU) 170, a current-control-unit (CCU) 172, a current-sense-unit (CSU), a series sense resistor, R, and electrotransport electrodes 132 and 134. The electrode 132 contains a suitable therapeutic drug or other agent 136 for delivery by electrotransport.

The DMCU 160 may be another MC68HC705K1 8-bit micro-controller and the DTU 170 and DRU 168 may be another pair of TMS3647 devices configured as a remote-control transmitter and receiver, respectively.

A low voltage power source, such as one or more 3-volt lithium coin cell batteries (MnO$_2$/Li) or the like may be used as the power supply for the delivery unit 130. Lithium coin cells are well known in the art and are available from several commercial sources, such as Panasonic, Matsushita, and Duracell. Power and ground connections for the control unit 130 are made in a conventional manner.

The DRS 164 receives the signal 120 from the CTS 154 transmitter. The DRS 164 is configured as an AM receiver to amplify, detect and demodulate the signal 120 and convert it to an output signal connected to the remote-control receiver unit DRU 168. The output signal from the DRS 164 is connected to the TIME input of the DRU 168. DRU 168 is programmed as a Valid Transmission Receiver (VTR) as described in the TMS3637 data sheet, op cit. The VTR programmed DRU 168 is responsive to the same code transmitted by the CTS 154. The VTR response is programmed to produce a high level signal on the OUT pin of the DRU 168 as long as the transmitted signal 120 continues to provide the transmitted 22-bit code. The OUT pin of DRU 168 is connected to the IRQ\' pin of the DMCU 160. The IRQ\' pin of DMCU 160 is programmed to generate a high level output on the PA1\' pin as long as the OUT logic level from DRU 168 is high. The high level on PA1\' corresponds to a demand for delivery of electrotransport current, I.

The output PA1\' of DMCU 160 connects to an input 176 of the electric current supply unit (ECU) 172. The ECU 172 may be configured as a constant (or non-constant) current source responsive to a high level on the input 176. The ECU 172 includes a source current output connection 178 and source current return connection 180. The ECU 172 is adapted to provide sufficient current, I, to drive the therapeutic agent 136 contained in electrode 132 into the patients' skin. The return electrode 134 is connected to one side of the sense resistor R. The other side of the sense resistor R provides a return path for the current I to the return connection 180 of ECU 172.

The current sense unit (CSU) 174 is connected across the sense resistor R by sense pins 182 and 184. The CSU 174 is configured to provide a high level signal on output 186 if the current I through the resistor R produces a voltage less than a predetermined amount for the dose rate desired. This may occur if the resistance of the patients' skin is too high such that the CSU 174 comes out of compliance or the electrodes become dislodged from the skin. In either case the ECU 172 will not be able to supply the necessary current and the desired dose will not be delivered. The output 186 is connected to an input PA2\' of DMCU 160. The PA2\' input is programmed as an active high input. In the event that CSU 174 senses the current, I, is not in compliance, the high level output signal 186 is received by the DMCU 160 input PA2\'.

A more detailed description of a suitable electrical current source ECU 172 and current sense unit CSU 174 may be found in previously filed patent application "Electrotransport Delivery Device Having Improved Safety and Reduced Abuse Potential" by McNichols et al, U.S. patent application Ser. No. 08/312,336 filed Sep. 26, 1994.

The DMCU 160 is programmed to provide a low level on an output PA6\' when the input signal PA2\' from output signal 186 is a high level and the PA1\' signal is high. This indicates that the desired electrotransport current, I, is not being delivered as desired.

Output PA6\' connects to the TIME input of the DTU 170. The DTU 170 is configured as a remote-control transmitter as described in the TMS3637 data sheet op cit. The DTU 170 is programmed to transmit a second 22-bit coded signal on the DTU 170 OUT pin when the Time input of DTU 170 is low. The second coded signal on OUT pin of DTU 170 is connected to an input of DTS 166. DTS 166 may also be configured as an AM transmitter stage converting the OUT signal 170 to an AM modulated RF signal 122 at a suitable carrier frequency of about 310 MHz. DTS 166 modulates the second 22-bit coded OUT signal 170 and transmits the second coded RF signal 122.

The second coded RF signal 122 is received by CRS 158 of the control unit 102. CRS 158 is configured as an AM receiver to detect, demodulate and amplify the received RF signal 122 and present the demodulated output to the TIME input of CRU 156.

The CRU 156 is configured as a receiver, as described in the TMS3637 data sheet, responsive to the same code programmed in the DTU 170. Upon receiving the demodulated second coded signal 122 from CRS 158, CRU 156 provides an output on the OUT pin of CRU 156. The OUT pin of CRU 156 connects to another programmed input pin of the MCU 150, for example, PA7. The input PA7 of the MCU 150 is programmed to be an input responsive to the OUT signal of CRU 156. The MCU 150 is programmed to provide an indication to the operator that the current, I, is not in compliance by toggling the pins PA3 and PA4 thereby flashing the LED 112 and/or sounding the annunciator 114 with a predetermined pattern. The operator may then act appropriately by checking the connection of the electrodes 132 and 134, or locating them to an area which makes better contact with the patient's skin.

From the foregoing description of the sense resistor R, ECU 172, CSU 174 and DMCU 160, those skilled in the art will readily appreciate that any number of patient body parameter conditions and/or delivery unit 130 conditions can be checked and transmitted to the remote control unit by means of DTS 166 and CRS 158. For example, means for sensing a body parameter such as a thermometer for sensing body temperature, a piezo electric device for sensing body or muscle movement, a blood glucose sensing element, and/or a blood gas sensing element may be substituted for the sense resistor R and associated circuitry in order to provide other types of sense signals relating to the particular parameter being sensed. In addition, means for sensing a parameter of the delivery unit 130 may also be sensed and transmitted in a similar fashion. For example, a counter which counts the number of doses delivered from the delivery unit 130 may transmit this dosing information. Other system parameters such as battery strength, amount of therapeutic agent remaining to be delivered, whether the delivery unit is currently operating in an "on" or an "off" mode, and whether or not a system malfunction has occurred could also be sensed by an appropriate sensing means and transmitted via the transmitting and receiving means.

In other embodiments of the electrotransport telemetry system in accordance with this invention, MCU 150 may be programmed with a plurality of control programs, as is well known in the art. The plurality of programs, may include providing multiple patterns of delivery. For example, one program may provide an output signal on the PA6 output to the TIME input of the CTU 152 having a sequence of predetermined periods such as 10 minutes of delivery followed by 50 minutes of non-delivery. This pattern may be repeated by a desired number of repetitions, as programmed. Any number of delivery profiles may be programmed into MCU 150. Alternatively, a program may choose different delivery and non delivery intervals and repetition sequences to be selected by differing actuation of the input switches 104–110.

The MCU 150 may also be programmed to react in predetermined fashion to signals received from the CRS 158 and CRU 156. For example, one program may provide alternative display patterns on the annunciator 114 or LED 112 in response to signals transmitted by DTS 166 and DTU 170, by flashing or sounding at a rapid rate to indicate an abnormal condition (eg, too low or too high a drug delivery rate) regarding the drug delivery.

It is contemplated that the embodiments of the invention may be combined in various combinations to provide, for example, a dosage regimen having a predetermined pattern customized by the physician for a particular patient, that is programmed into the control unit 102.

The inputs IRQ\, PA0, PA1, PA2, of the control unit 102, connected to control switches 104–110, could be programmed to provide different optional dosage patterns on patient demand. The delivery unit 130 could be configured with different sensor circuitry having signals responsive to other conditions, such as the oxygen or carbon dioxide content of the patient's tissue, heart rate, skin impedance, skin temperature and the like. These signals may be fed back to the control unit 102 by means of the telemetry link of this invention providing a compact delivery unit in a system having improved performance. Other embodiments of this invention incorporating numerical displays, such as multiplexed LCD displays connected to the MCU 150, are contemplated as within the scope of the claims.

While the foregoing detailed description has described an embodiment of the electrotransport system having a telemetry link communicating between control and delivery units in accordance with this invention, it is to be understood that the above description is illustrative only and not limiting of the disclosed invention. It will be appreciated that it would be possible to modify the number and type of control circuits and delivery circuits, the materials and methods of construction and the logic forms and interconnections or to include or exclude various elements within the scope and spirit of the invention. Thus the invention is to be limited only by the claims as set forth below.

We claim:

1. In an electrotransport system for delivering a therapeutic agent through a body surface of a patient, the system including a delivery unit having a pair of electrodes, at least one of the electrodes containing the therapeutic agent to be delivered, a source of electrical power electrically connectable to the electrodes, and a control unit for communicating with the delivery unit, the improvement comprising:

the delivery unit being physically remote from the control unit; and a telemetry communication link between the delivery and control units whereby the units communicate through a radiated energy signal transmitter and a receiver.

2. The electrotransport system of claim 1, wherein the control unit comprises the transmitter and the delivery unit comprises the receiver.

3. The electrotransport system of claim 1, wherein the delivery unit comprises the transmitter and the control unit comprises the receiver.

4. The electrotransport system of claim 1, wherein the delivery unit comprises both a radiated energy signal transmitter and receiver and the control unit comprises both a radiated energy signal transmitter and receiver.

5. The electrotransport system of claim 1, wherein the control unit controls an electrotransport current applied to the patient.

6. The electrotransport system of claim 1, wherein the control unit is adapted to be mounted on a wrist of the patient.

7. The electrotransport system of claim 1, wherein the control unit operates and transmits the radiated energy signal to the receiver from a distance of several centimeters to thousands of kilometers.

8. The electrotransport system of claim 1, wherein the transmitter comprises a manually operated switch.

9. The electrotransport system of claim 1, wherein the control unit includes a microprocessor having an output connected to the transmitter, the microprocessor having a plurality of stored programs for providing a corresponding plurality of radiated energy signals; and means for selecting one of said stored programs to provide a selected program;

whereby the delivery of the therapeutic agent is remotely controlled according to the radiated energy signal corresponding to the selected program.

10. The electrotransport system of claim 1, wherein the transmitter and receiver are adapted to communicate by radio frequency radiated energy.

11. The electrotransport system of claim 10, wherein the radio frequency radiated energy has a frequency of about 1 MHz to 1000 MHz.

12. The electrotransport system of claim 10, wherein the radio frequency radiated energy is modulated by a modulator selected from the group consisting of an amplitude modulator, a frequency modulator, a frequency shift key, and a phase shift key.

13. The electrotransport system of claim 1, wherein the radiated energy is selected from the group consisting of ultrasonic, optical, infrared and electromagnetic induction energies.

14. The electrotransport system of claim 1, wherein the transmitter includes a coder for coding the transmitted signals and the receiver includes a decoder for decoding the transmitted signals.

15. The electrotransport system of claim 1, wherein the delivery unit includes:

a sensor for sensing a predetermined patient body parameter condition, the sensor providing a sense signal; and a radiated energy return transmitter responsive to the sense signal, for transmitting a return radiated energy signal; wherein the control unit includes a receiver and display for receiving the return radiated energy signal and providing a display of the body parameter condition.

16. The electrotransport system of claim 15, wherein the sensor is adapted to sense a body parameter selected from the group consisting of breathing rate, body temperature, muscle movement, blood glucose concentration, sweat response, skin resistance, heart rate, tissue oxygen content, tissue carbon dioxide content, patient emergency condition and body motion.

17. The electrotransport system of claim 15, wherein the display is selected from the group consisting of a light emitting diode, a liquid crystal display, an audio annunciator, a cathode ray tube display, a video screen and a printer.

18. The electrotransport system of claim 1, wherein the delivery unit includes:

a sensor for sensing a predetermined electrotransport system parameter condition, the sensor providing a sense signal; and a radiated energy return transmitter responsive to the sense signal, for transmitting a return radiated energy signal; wherein the control unit includes a receiver and display for receiving the return radiated energy signal and providing a display of the system parameter condition.

19. The electrotransport system of claim 18, wherein the sensor senses a system parameter selected from the group consisting of therapeutic agent dosing history, amount of therapeutic agent remaining to be delivered, battery strength, geographic location of the delivery unit, whether the delivery unit is currently delivering therapeutic agent, and system malfunction.

20. The electrotransport system of claim 1, wherein the delivery unit comprises a receiver for receiving a radiated energy signal and providing a control signal responsive to the radiated energy signal and a current controller for controlling an electrotransport current applied by the delivery unit, the controller being responsive to the control signal; and the control unit comprises a transmitter means for transmitting the radiated energy signal, whereby the electrotransport current applied by the delivery unit is controlled by the radiated energy signal transmitted from the remote control unit.

21. The electrotransport system of claim 1, the control unit including a magnetically activated switch which when closed enables communication between the delivery and control units.

* * * * *